United States Patent
Markman

(10) Patent No.: US 9,050,177 B2
(45) Date of Patent: *Jun. 9, 2015

(54) METHOD AND APPARATUS FOR A PROCESS CREATING AN INTERNAL TISSUE GRAFT FOR ANIMAL AND HUMAN RECONSTRUCTIVE PURPOSES

(71) Applicant: Barry Markman, Las Vegas, NV (US)

(72) Inventor: Barry Markman, Las Vegas, NV (US)

( * ) Notice: Subject to any disclaimer, the term of this patent is extended or adjusted under 35 U.S.C. 154(b) by 242 days.

This patent is subject to a terminal disclaimer.

(21) Appl. No.: 13/687,082

(22) Filed: Nov. 28, 2012

(65) Prior Publication Data

US 2013/0085579 A1  Apr. 4, 2013

Related U.S. Application Data

(63) Continuation of application No. 13/101,022, filed on May 4, 2011, now Pat. No. 8,858,647.

(60) Provisional application No. 61/331,805, filed on May 5, 2010.

(51) Int. Cl.
*A61F 2/02* (2006.01)
*A61F 2/06* (2013.01)

(52) U.S. Cl.
CPC .. *A61F 2/02* (2013.01); *A61F 2/062* (2013.01)

(58) Field of Classification Search
CPC .............. A61F 2/02; A61F 2/06; A61F 2/062
USPC ................... 623/23.72, 23.15, 23.51
See application file for complete search history.

(56) References Cited

U.S. PATENT DOCUMENTS

| 4,950,296 | A | 8/1990 | McIntyre |
|---|---|---|---|
| 5,728,159 | A | 3/1998 | Stroever et al. |
| 5,759,205 | A | 6/1998 | Valentini |
| 6,911,220 | B1 | 6/2005 | Sachs |
| 6,949,252 | B2 | 9/2005 | Mizuno et al. |
| 7,066,962 | B2 | 6/2006 | Swords |
| 7,189,259 | B2 | 3/2007 | Simionescu et al. |
| 7,282,165 | B2 | 10/2007 | Williams, III et al. |
| 7,416,546 | B2 | 8/2008 | Pugsley et al. |
| 7,427,284 | B2 | 9/2008 | Seedhom et al. |
| 7,458,975 | B2 | 12/2008 | May et al. |
| 7,520,898 | B2 | 4/2009 | Re et al. |
| 7,572,298 | B2 | 8/2009 | Roller et al. |
| 7,645,568 | B2 | 1/2010 | Stone |
| 7,723,108 | B2 | 5/2010 | Truncale et al. |
| 7,727,278 | B2 | 6/2010 | Olsen et al. |
| 7,776,089 | B2 | 8/2010 | Bianchi et al. |
| 7,815,923 | B2 | 10/2010 | Johnson et al. |
| 8,500,740 | B2 | 8/2013 | Bojarski et al. |
| 8,597,687 | B2 | 12/2013 | Daniel |
| 8,858,647 | B2 * | 10/2014 | Markman ................. 623/23.72 |
| 2004/0082063 | A1 | 4/2004 | Deshpande et al. |
| 2007/0061015 | A1 | 3/2007 | Jensen et al. |
| 2009/0291116 | A1 | 11/2009 | Casellas |
| 2010/0137903 | A1 | 6/2010 | Lee et al. |
| 2010/0161032 | A1 | 6/2010 | Avellanet |
| 2011/0022171 | A1 | 1/2011 | Richter et al. |

* cited by examiner

*Primary Examiner* — Victor Nguyen

(74) *Attorney, Agent, or Firm* — Weide & Miller, Ltd.

(57) ABSTRACT

A method and apparatus is provided for creating an internal reconstruction tissue graft. Templates may be used to create a multitude of patterns in a variety of tissue reconstruction grafts. An apparatus may be used to create an internal tissue graft for reconstruction through either compression and/or removal of segments. An apparatus may be used, through either compression and or removal of segments of a preformed template made of synthetics and or metal that mirrors a template that can be used as an internal tissue graft for reconstruction. In a method, such as using software analysis and an apparatus, the physical properties of the tissue graft and its pre- and post-operative properties and appearance may be measured.

17 Claims, 1 Drawing Sheet ion Ser. No. 13/101,022, filed May 4, 2011, and claims
METHOD AND APPARATUS FOR A PROCESS CREATING AN INTERNAL TISSUE GRAFT FOR ANIMAL AND HUMAN RECONSTRUCTIVE PURPOSES

RELATED APPLICATION DATA

This application is a continuation of U.S. patent application Ser. No. 13/101,022, filed May 4, 2011, and claims priority to U.S. Provisional Application Ser. No. 61/331,805, filed May 5, 2010.

FIELD OF THE INVENTION

The present invention relates to a device and method creating a novel surgical internal reconstruction tissue graft by creating template designs on internal reconstructive grafts and measuring their physical properties.

BACKGROUND OF THE INVENTION

Current surgical reconstruction of internal tissue defects utilizes a solid, porous sheet with or without perforations. Current grafts allow for perforations that do enhance fluid egress and in growth of new tissue but due to the constrictive nature of such tissue grafts, the incidences of recurrences and the inability to expand with the application of increased pressure has allowed for a significant incidence of recurrence, stress tears, and an inability for expansion used in reconstructive and aesthetic procedures. Current tissue grafts also do not allow for the ability to enhance traction between the graft and specific anatomic points, similar in physical properties of how specific tread designs enhance traction between the tire and the road surface, as well as increase the time of utilization of the tire. The current novel invention applies these engineering applications to achieve similar results to internal surgical tissue grafts. None of the references below discuss the advantages of utilizing the current method and apparatus of applying designs and templates to internal surgical reconstructive grafts.

SUMMARY OF THE INVENTION

Figure 1A:
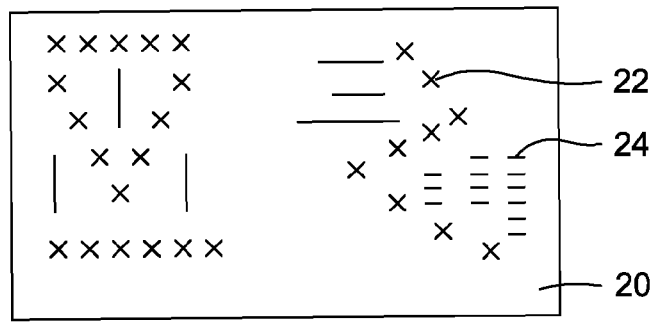
FIGS. 1A and 1B illustrate a top and bottom, respectively, of a tissue graft having patterns in accordance with the invention.

A method and apparatus for creating an internal reconstruction tissue graft is disclosed. In one embodiment, the method and apparatus comprises the following components and variations thereof: 1) a method for the creation of templates used to create a multitude of patterns in a variety of tissue reconstruction grafts; 2) an apparatus that through either compression and or removal of segments of tissue create the internal tissue graft for reconstruction; 3) an apparatus that through either compression and or removal of segments of a preformed template (such as made of synthetics and or metal) that mirrors a template that can be used as an internal tissue graft for reconstruction; and/or 4) a method of measuring, through software analysis and an apparatus, the physical properties of the tissue graft and its pre and post-operative properties and appearance.

The purpose in creating a template with variable and multiple patterns throughout a single sheet preferably enables the tissue graft and its incorporation in an anatomic area.

In one embodiment, the invention is configured to, and an advantage of the invention comprises, reducing stress in grafts subject to continuous motion, such as, in the knee, hip, and cervical regions In one embodiment, the invention is configured to, and an advantage of the invention comprises, reducing stress in grafts subject to increased pressure gradients such as in the abdominal wall, inguinal hernia, and arterial grafts.

In one embodiment, the invention is configured to, and an advantage of the invention comprises, allowing for selective expandability (such as via partial or non-through expansion incisions and/or through expansion incisions of various thicknesses in the graft) in order to achieve better contour and external appearance.

In one embodiment, the invention is configured to, and an advantage of the invention comprises, allowing for selective expandability (such as via partial or non-through expansion incisions and/or through expansion incisions of various thicknesses in the graft) in order to achieve better outflow of blood in venous grafts.

In one embodiment, the invention is configured to, and an advantage of the invention comprises, allowing for selective traction or adhesion points of tissue grafts to key anatomic areas when needed in order to increase fixation at insertions and origins to reduce slippage of the graft.

In one embodiment, the invention is configured to, and an advantage of the invention comprises, promoting vascular in growth of the body's tissue in specific areas of the internal tissue graft.

In one embodiment, the invention is configured to, and an advantage of the invention comprises, allowing for an increase in the period of time of utilization and longevity of the internal reconstructive graft.

Further objects, features, and advantages of the present invention over the prior art will become apparent from the detailed description of the drawings which follows, when considered with the attached figures.

DETAILED DESCRIPTION OF THE INVENTION

One embodiment of the invention comprises a method of creating templates used to create a multitude of patterns in a variety of tissue reconstruction grafts. Such may consist of pre- or intra-operatively made templates.

In one embodiment, the templates may be based on software analysis of an initial tissue defect, the template designed to allow for a desired graft pattern to reduce the potential pressure, reduce stress, decrease wear and tear, and/or provide traction between a created graft and specific anatomic points. Based on factors such as, but not limited to, the size, shape, thickness, width, variegations, type, and the desired surgical outcome, a pattern may be created within the internal tissue graft. Due to the variability in a defect being reconstructed, such as the Abdominal Wall, Breast, Face, and Extremities, different template patterns may be generated. Software analysis may be used to create an appropriate internal tissue graft for an identified existing defect.

In one embodiment, different materials may be used to make the templates and their respective patterns. Currently external reconstructive templates use a mesh pattern with expansion ranging from 1 to 2, 1 to 4, 1 to 8 etc. In a preferred embodiment of the invention, internal reconstruction grafts may be created which not only permit mesh expansion, but provide for a multitude of various designs, shapes, patterns, variegations and materials to accommodate the existing defect to achieve the desired reconstructive and aesthetic results.

In one embodiment, software and/or hardware may be used to perform a pre-operative analysis. Templates may be constructed from a pre-made mold, and be made of different materials such as metal or plastic to be integrated with a compression device. The template can be integrated with a stationary or portable compression apparatus that can create prepackaged tissue grafts to be subsequently sterilized to be used by a surgeon in the operating room, or portable temples and compression devices can be used in a sterile operation room, or an apparatus may allow a surgeon to incise predetermined patterns into the tissue grafts by a knife or other cutting implement. A primary objective of the invention allows for newly created internal patterned tissue grafts to accommodate anticipated problems due to any and all activity and reconstructive and aesthetic results.

In one embodiment, an apparatus, either via compression and/or removal of segments of tissue, creates an internal tissue graft for reconstruction by creating a desired pattern within an internal tissue graft. Compression can be used against the template that in turn creates the desired internal pattern.

In a second methodology, pre-designed patterns of tissue mirror the specific designs on a pre-formed template that can be subsequently used on a portable compression and punch apparatus that can used to create the internal tissue graft in the operating room. Additional techniques using an apparatus that uses laser cutting technology can be utilized.

Figure 1B:
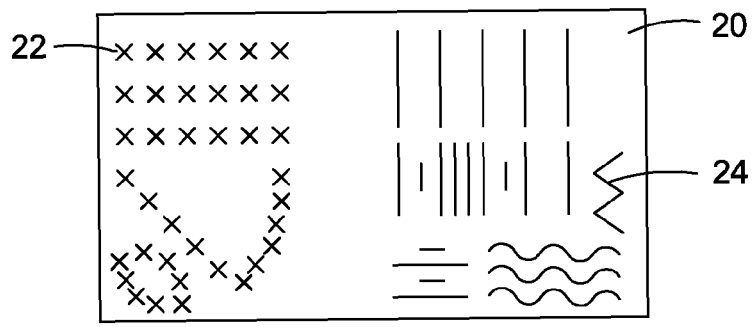
Figure 2:
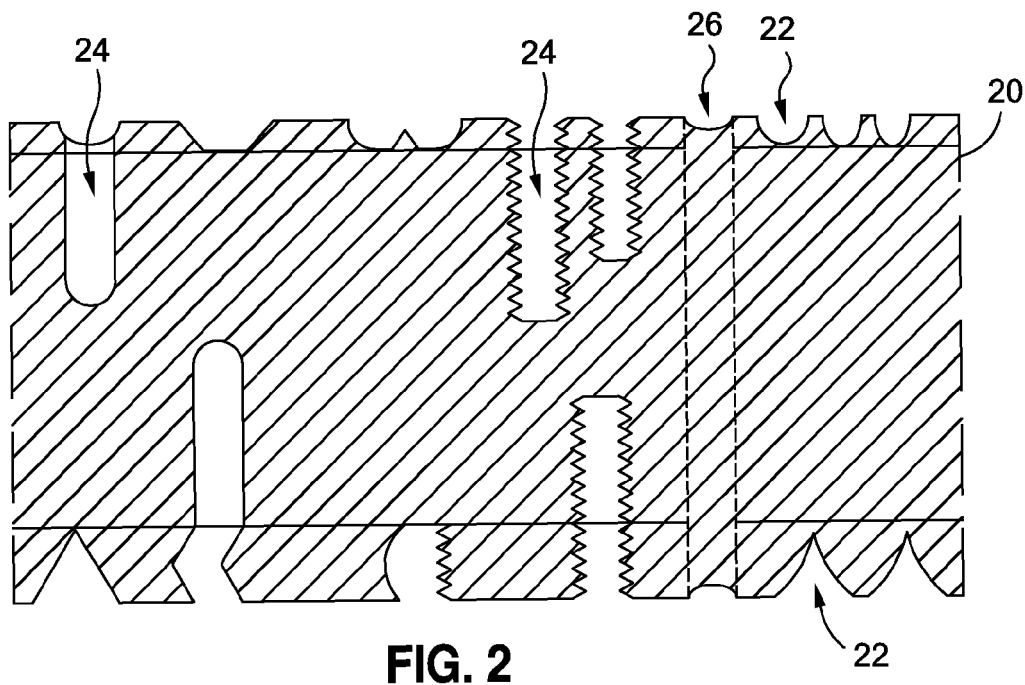
FIG. 2 is a side view of a tissue graft having various adhesion, expansion and through-hole features in accordance with the invention.

For example, FIG. 2 illustrates a tissue graft 20 where compression and/or removal of segments (such as spaced or separated by various distances between them) create recessed expansion patterns of various depths and shapes 22, adhesion projections of various heights and shapes 24 and through holes 26. FIGS. 1A and 1B illustrate one example of patterns of adhesion features 22 and expansion features 24 relative to a top (in FIG. 1A) and bottom (in FIG. 1B) of a tissue graft 20, which patterns may be used to generate a tissue graft having particular desired characteristics for a particular application.

Current medical devices are not applicable for creating the multitude of desired pattern grafts for each defect. In accordance with the invention, an apparatus can be used to create patterns applicable to a specific tissue defect, whether pre- or intra-operatively.

Measuring, such as through software analysis and an apparatus, the physical properties of the tissue graft and its pre- and post-operative appearance may be utilized to correlate the physical properties of a created internal tissue graft and desired reconstructive and aesthetic grafts.

Broadly the present invention is directed to methods, apparatus, and devices involving variable templates for the purpose of internal reconstruction of body tissues including, but not limited to, a breast, the abdominal wall, vascular, and extremities. In a first method in accordance with the present invention, a template is created that allows for increased flexibility as it relates to the graft, and subsequently the need to contouring to sling a breast implant used in achieving a natural result for the patient. The template is pre-made or created during the reconstruction procedure to enhance the physical properties of the internal tissue graft to meet the requirements of the tissue grafts expectations, whether it is enhanced expansion, flexibility, traction, or period of utilization in anatomic areas where it is placed.

The above description represents one embodiment of the present invention. However, many variations to the method and apparatus are possible without deviating from the scope of the invention. It will be understood that the above described arrangements of apparatus and the method described herein are merely illustrative of applications of the principles of this invention and many other embodiments and modifications may be made without departing from the spirit and scope of the invention as defined in the claims.

What is claimed is:

1. A method of using one or more templates to create an anatomically designed reconstructive tissue constructive graft for implantation at an anatomical site of a human body, comprising the steps of:
   (a) collecting information regarding characteristics of an anatomical site of a human body at which an internal tissue graft is needed;
   (b) determining desired characteristics of a reconstructive tissue graft for said anatomical site from said collected information;
   (c) obtaining a tissue graft from a location different than said anatomical site; and
   (d) utilizing a template to create a reconstructive tissue graft by compressing, cutting or removing portions of said tissue graft using said template to change a natural surface of a tissue graft to include a plurality of different surface patterns which cause said reconstructive tissue graft to have said desired characteristics for said anatomical site.

2. The method according to claim 1, wherein said tissue graft comprises human tissue.

3. The method according to claim 1, wherein said tissue graft comprises cellular non human tissue, including cellular and acellular processed grafts.

4. The method according to claim 1, wherein said tissue graft comprises one or more synthetic materials.

5. The method according to claim 1, wherein at least one of said plurality of different surface patterns is configured to permit the egress of fluid from said anatomical site.

6. The method according to claim 1, wherein said tissue graft has a thickness and wherein said plurality of different surface patterns may be either full thickness or partial thickness.

7. The method according to claim 1, wherein said tissue graft has an anterior surface and a posterior surface and said plurality of surface patterns are associated with both said anterior and posterior surfaces.

8. The method according to claim 1, wherein at one least one of said plurality of different surface patterns is configured to permit controlled expansion of said reconstructive tissue graft.

9. The method according to claim 1, wherein at least one of said plurality of different surface patterns is configured to provide enhanced stress relief during motion of and reduction of internal pressure on the reconstructive tissue graft.

10. The method according to claim 1, wherein at least one of said plurality of different surface patterns is configured to provide enhanced adhesion between the reconstructive tissue graft and tissue at said anatomical site.

11. The method according to claim 1, wherein at least one of said plurality of different surface patterns is configured to provide enhanced retention of various medicants and materials.

12. The method according to claim 1, wherein at least one of said plurality of different surface patterns comprises variegations.

13. The method according to claim 1, wherein at least one of said plurality of different surface patterns is configured to facilitate placement by sutures or staples of the reconstructive tissue graft at said anatomical site.

14. A method for creating an pre configured anatomically designed reconstructive tissue graft for implantation at an anatomical site of a human body, comprising the steps of:
   (a) collecting information regarding characteristics of an anatomical site of a human body at which an internal tissue graft is needed;
   (b) determining desired characteristics of a reconstructive tissue graft from said collected information;
   (c) obtaining a tissue graft from a location different than said anatomical site; and
   (d) utilizing an apparatus having a configuration which is dependent upon said desired characteristics to compress, cut or remove portions of said tissue graft to change a natural surface of said tissue graft to create a reconstructive tissue graft having a plurality of different surface patterns, said surface patterns designed to enhance retention of medicants and materials.

15. The method according to claim 14, wherein said tissue graft comprises human tissue.

16. The method according to claim 14, wherein said tissue graft comprises cellular non human tissue, including cellular and acellular processed grafts.

17. The method according to claim 14, wherein said tissue graft comprises one or more synthetic materials.

* * * * *